United States Patent [19]

Kondo

[11] Patent Number: 4,694,821
[45] Date of Patent: Sep. 22, 1987

[54] AIR FEED CONTROL DEVICE FOR AN ENDOSCOPE

[75] Inventor: Mitsuo Kondo, Saitama, Japan

[73] Assignee: Fuji Photo Optical Co., Ltd., Saitama, Japan

[21] Appl. No.: 790,481

[22] Filed: Oct. 23, 1985

[30] Foreign Application Priority Data

Oct. 24, 1984 [JP] Japan ............................ 59-159793[U]

[51] Int. Cl.$^4$ ............................................... A61B 1/12
[52] U.S. Cl. ........................................................ 128/4
[58] Field of Search ......................................... 128/4, 6

[56] References Cited

U.S. PATENT DOCUMENTS 4,261,343 4/1981 Ouchi et al. ............................ 128/4

Primary Examiner—William H. Grieb
Attorney, Agent, or Firm—Young & Thompson

[57] ABSTRACT

An air feed control device for an endoscope for feeding air into a body cavity, comprises a regulating valve device including therein separate channels for air inflow and air outflow and a vent opening to the atmosphere. The air channels communicate with each other only via a hole which is disposed in the vicinity of the vent opening to the atmosphere so as to prevent the air resistance of the open vent from forcing air into the outlet air pipe and then into the body cavity.

11 Claims, 7 Drawing Figures

AIR FEED CONTROL DEVICE FOR AN ENDOSCOPE

BACKGROUND OF THE INVENTION

1. Field of the Invention

The present invention relates to an air feed control device for an endoscope which is used to regulate the amount of air to be fed into a cavity such as a cavity of a human body.

2. Description of the Prior Art

Conventional endoscopes are usually equipped with an air feed control device which is adapted to regulate the quantity of air to be fed into a cavity such as a cavity of a human body and which is usually combined with a water feed device for cleaning the objective lens or its cover glass at the distal end of the insertion section of the endoscope to remove soil thereon. Air can also be used to blow off drops of water remaining on the objective lens or cover glass.

There have been proposed air feed control devices of the type having valve means provided with an air vent passage opening to the atmosphere which is adjustably closed by the bulb of a finger of an operator in order to regulate the quantity of air escaping from the vent passage into the atmosphere and hence the quantity of air introduced into the cavity through the air feed nozzle.

A problem in the majority of air feed control devices at present on the market is that even if the vent passage is fully opened in order to bypass air feed from the body cavity, a part of the air is still forced into the body cavity because it is impossible to allow air to escape through the vent passage without giving rise to resistance.

Reference may be made to the following description from which the present state of the art is clearly apparent.

FIG. 7 schematically shows an air feed-water feed control device at present on the market in which a regulating valve means 10 is mounted in the operating section 1 of the endoscope. Valve means 10 selectively connects an intake air pipe $4_2$ having its one end connected to an air supply (which is well known in the art and not shown) provided separately from the endoscope, with an outlet air pipe $4_1$ connected to an air feed-water feed nozzle 3 at the distal end of the flexible insertion section 2. Flexible section 2 is insertable into a body cavity.

The regulating valve 10 is also so arranged as to be capable of selectively connecting an intake water pipe $5_2$ having its one end connected to a water supply (which is also well known in the art and not shown therein) provided separately from the endoscope, with an outlet water pipe $5_1$ with its one end connected to the air feed-water feed nozzle 3. One-way valve 8 prevents the counterflow of air.

Specifically, the regulating valve means 10 comprises a valve casing 9 having the shape of a barrel with a cylindrical bore, and a valve body 6 having a vent passage 6' slidably airtightly fitted in the valve casing 9. Within the bore is housed a helical compression spring 7 which continuously urges the valve body 6 up as seen in FIG. 7, so that the intake and outlet air pipes $4_2$, $4_1$ communicate by the regulating valve means 10. The valve body 6 is further provided with an annular groove 6" around its outer periphery at the axial position where the annular groove 6" is aligned with both of the intake and outlet water pipes $5_1$, $5_2$ when the valve body 6 is pushed down against the helical compression spring 7.

As seen in FIG. 7, the valve body 6, when forced up, allows the air collected in the valve casing 9 to escape into the atmosphere through the vent passage 6'.

In the air feed-water feed control device of the above-mentioned type, for the sake of sufficient air feed into the body cavity, the vent passage 6' of the valve body 6 is blocked by completely closing its open end with the bulb of a finger after starting the air supply such as an air pump, the whole quantity of the air collected in the valve casing 9 flows into the outlet air pipe $4_1$, and consequently a jet of air is fed into the body cavity as well as shot against an objective lens from the air feed-water feed nozzle 3.

Then, gradually opening the open end of the vent passage 6' by moving the finger either upwardly or laterally, the quantity of air escaping into the atmosphere increases in accordance with the degree of the opening.

On the other hand, when the valve body 6 is pushed down against the helical compression spring 7 until the annular groove 6" is aligned with both of the intake and outlet water pipes $5_2$, $5_1$, then the communication between the intake and outlet air pipes $4_2$, $4_1$ is interrupted by the bottom part of the valve body 6 so as to stop the jet of air from the air feed-water feed nozzle 3. Simultaneously, water from the intake water pipe $5_2$ flows through the annular groove 6" into the outlet water pipe $5_1$ and a jet of water is shot against the objective lens.

In the event of intending to expel all of the air which has collected in the valve casing 9, a part of this air is forced to flow into the outlet air pipe $4_1$ and thence into the body cavity from the air feed-water feed nozzle 3.

The reason why the whole quantity of air does not always escape into the atmosphere through the vent passage 6' is that the vent passage 6' imposes resistance against air flow therethrough.

OBJECT OF THE INVENTION

The object of the present invention is to overcome the disadvantages set forth in the foregoing and to provide an air feed control device which ensures the prevention of air flow into the body cavity when a regulating valve means is fully opened, and which is of simple design and is also inexpensive to manufacture.

SUMMARY OF THE INVENTION

To this end, the air feed control device in accordance with the invention for an endoscope comprises regulating valve means mounted in the operation section of the endoscope and having a vent opening to the atmosphere, an intake air pipe having its one end adapted to be connected to an air supply provided separately from the endoscope, and an outlet air pipe with its one end connected to an air feed nozzle at the distal end of the insertion section of the endoscope, said regulating valve means being so arranged as to be capable of connecting the intake and outlet air pipes in communication not only with each other but also with the atmosphere and of alternatively interrupting the communication therebetween.

The distinctive feature of the air feed control device in accordance with the invention lies in the fact that the regulating valve means includes separate channels for air inflow and air outflow which are disposed between the vent opening and the intake air pipe, and the outlet air pipe, respectively, and that the air channels are in communication with each other in the vicinity of the vent opening.

Thus in the event of a completely opened vent opening, air from the intake air pipe, although resisted by the inflow channel, flows without impelling the air in the outflow channel as well as without a part of the air from the intake air pipe flowing into the outflow channel.

BRIEF DESCRIPTION OF THE DRAWINGS

Other features of the invention will be more apparent upon consideration of the following description in conjunction with the accompanying drawings, wherein.

DETAILED DESCRIPTION OF THE INVENTION

Because endoscopes are well known, the present description will be directed in particular to elements forming part of, or cooperating more directly with, the present invention, the endoscope elements not specifically shown or described herein being understood to be selectable from those known in the prior art.

Figure 1:
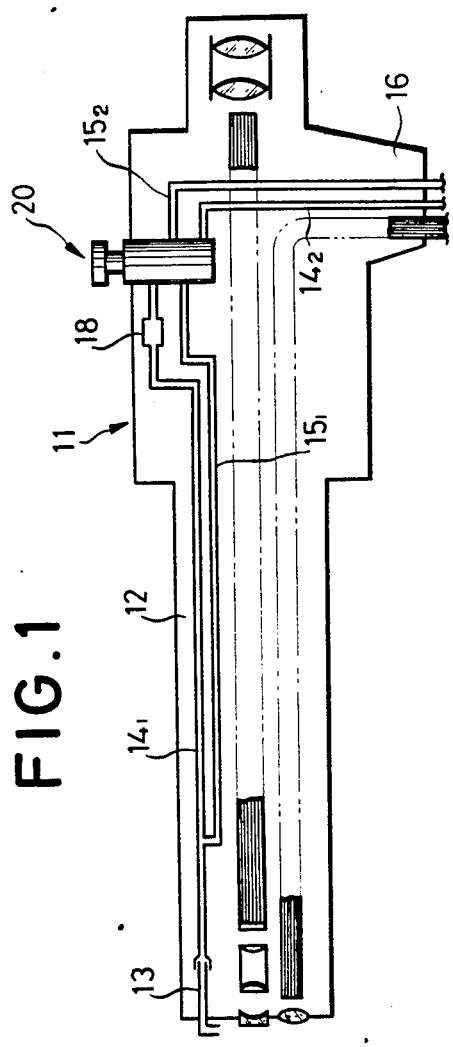
FIG. 1 is a schematic view of an endoscope to which is applied a first embodiment of an air feed control device, in combination with a water feed control device, in accordance with the present invention.
Figure 7:
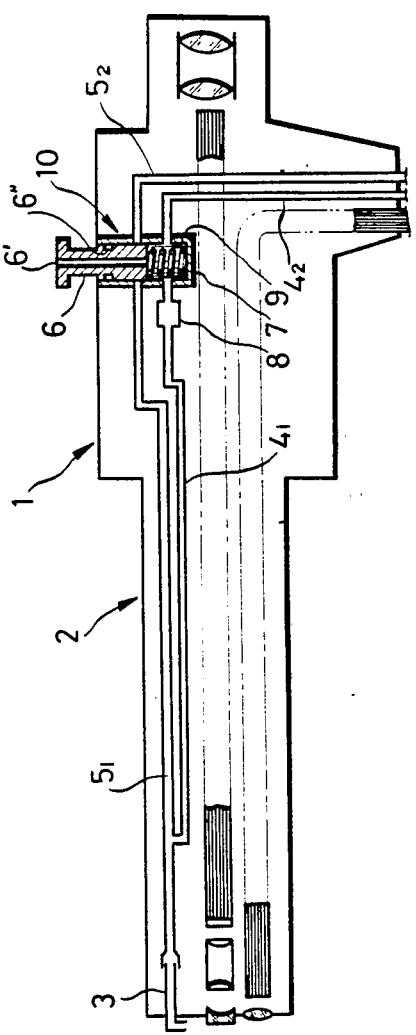
FIG. 7, as previously indicated, is a schematic view of an endoscope in which is installed a conventional air feed-water feed control device.
Figure 2:
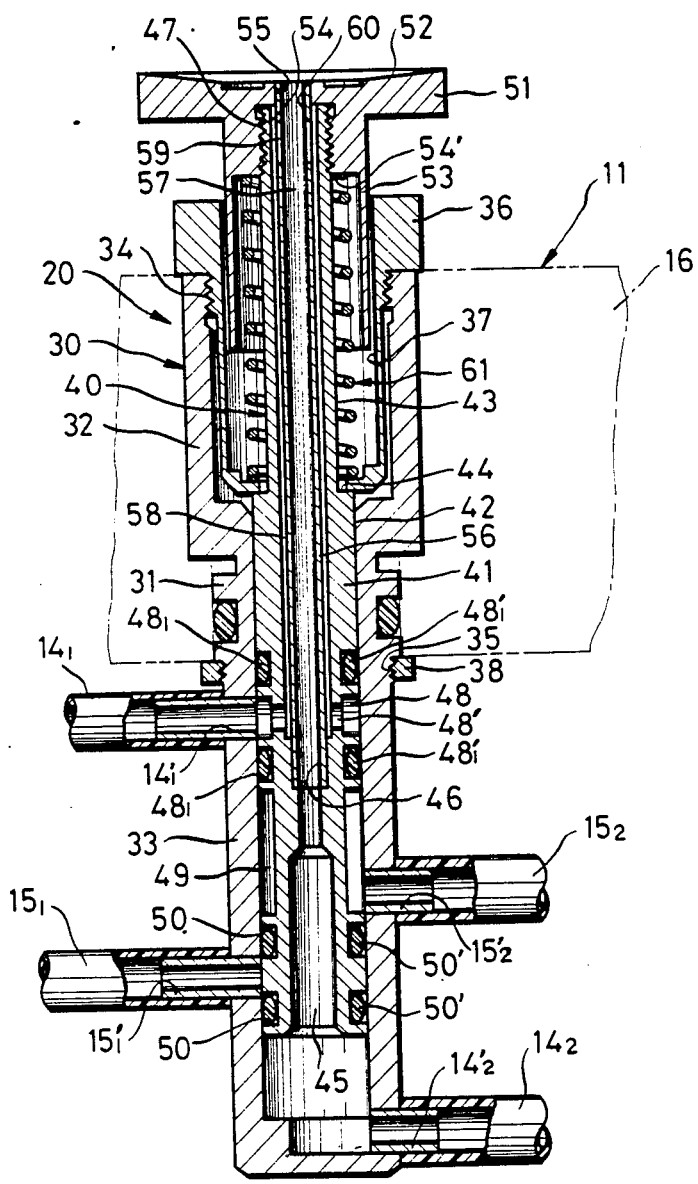
FIG. 2 is a longitudinal sectional view of the regulating valve means of the air feed control device of FIG. 1.

Referring now to FIG. 2, schematically shown therein is an endoscope to which is applied an air feed control device, according to the first embodiment of the present invention, of the type which is in combination with a water feed control device which is well known per se in the art.

Such an endoscope, as is well known in the art, generally comprises an operating section 11, an insertion section 12, insertable into a cavity such as a cavity of a human body, having a distal end where are disposed a light guide window glass, an image guide window glass, an air feed-water feed nozzle 13, a forceps/suction opening, and other elements, all of which are well known. A flexible tube section 16, in which are disposed a light guide, electric wires, pipes, etc., has a connector at its distal end to be connected to a separate control unit including a light source, and various control devices etc., which is well known in the art and hence not shown.

The air feed control device, which is in combination with a water feed device and referred to hereinafter to as air feed-water feed control device, comprises regulating valve means 20 mounted in the operation section 11 of the endoscope, an intake air pipe $14_2$ having its one end adapted to be connected to an air supply such as an air pump housed in the control unit, and an outlet pipe $14_1$ with its one end connected to the air feed-water feed nozzle 13, the intake and outlet air pipes being connected in communication with each other by the regulating valve means 20. The air feed-water feed control device also comprises an intake water pipe $15_2$ having its one end adapted to be connected to a water supply housed in the control unit and an outlet water pipe $15_1$ with its one end connected to the air pipe $14_1$ near the air feed-water feed nozzle 13, these water pipes $15_1$, $15_2$ being interconnected by the regulating valve means 20 so as to selectively be in communication with each other. One-way valve 18 prevents the counterflow of air.

The regulating valve means 20, as illustrated in more detail in FIG. 2, comprises a hollow body or valve casing 30 fixed to the wall 16 of the operation section 11 by means of an externally threaded hollow clamping bolt 36 and a nut 38.

The valve casing 30 has the shape of a barrel having an axial cylindrical bore comprising an upper bore portion 32 having a relatively large inner diameter and a lower bore portion 33 having a relatively small inner diameter. In the lower bore portion 33 a valve body assembly 40 is supported in airtight relation for axially sliding movement. On the other hand, within the upper bore portion 32 is housed a resilient system consisting of a helical compression spring 61, and part of an internally threaded end cap 51 which serves as a support for the spring 61 as well as providing a pushbutton which will be described in detail later. For fastening the valve casing 30 to the wall 16, the valve casing 30 is provided with internal threads 34 at its top and external threads 35 at its midportion, engageable with the hollow bolt 36 and the nut 38, respectively. The hollow bolt 36 has a downwardly extending, cylindrical skirt 37 with an inwardly extending circular flange which serves as a support for the spring 61.

Around the lower casing part 33 are provided joint pipes $14_1'$, $15_2'$, $15_1'$ and $14_2'$ to which are connected flexible pipes $14_1$, $15_2$, $15_1$ and $14_2$, in that order top to bottom.

The valve body assembly 40 comprises a main valve body 41 having the shape of a pipe having an elongated axial bore extending from its top to its bottom, a cylindrical partition wall 56 which is fitted airtightly into the end portion 46 of reduced inner diameter, of the elongated bore so as to provide an air channel 58 therebetween, and the pushbutton 51 which is screwed into the main valve body 41 at the threaded top end 47. More specifically, the main valve body 41 comprises a lower valve portion 42 which is supported airtightly in the bore of the lower portion 33 of the valve casing 30 for sliding movement, and an upper valve portion 43 having a reduced outer diameter so as to form at the top end of the lower valve portion 42 a shoulder 44 against which the circular flange of the skirt 37 of the clamping bolt 36 abuts. Around the periphery of the lower valve portion 42 is an annular groove 48 communicating with the air channel 58 by holes 48' just above the end portion 46 of the elongated bore of the main valve body 41, the annular groove 48 being so arranged as to align with the joint pipe $14_1'$ for providing communication between the air channel 58 and the outlet air pipe $14_1$ when the valve body assembly 40 is in its upper position shown in FIG. 2. The main valve body 41 is also provided with another annular groove 49 by which the intake and outlet joint pipes $15_1'$, $15_2'$ communicate when the valve body assembly 40 is forced down against the spring 61. On both sides of the outlet side joint pipes $14_1'$, $15_1'$, there are provided around the valve body 41 annular grooves $48_1$, 50 in which are disposed O-rings $48_1'$, $50'$ in order to achieve a sufficient degree of fluidtightness of the outlet side joint pipes $14_1'$, $15_1'$ connected to the valve casing 30.

The pushbutton 52 consists of a single piece T-shaped member which has a shallow concave head 52 and a downwardly extending cylindrical skirt 53 which is housed inside the cylindrical skirt 37 of the hollow bolt 36 so as to hold the spring 61 therebetween. The pushbutton 51 is provided with an internally threaded axial hole 54 into which is screwed the externally threaded top end 47 of the main valve body 41. Pushbutton 51 also has a reduced diameter opening 55 communicating with the hole 54. The upper end of the cylindrical partition wall 56 is sealingly fitted in opening 55 and provides a vent opening 60 which is adjustably closed by the bulb of a finger in order to regulate the quantity of air to be fed into a body cavity.

In the vicinity of the vent opening 60, there is provided in the cylindrical partition wall 56 a hole 59 communicating between the inner and outer air channels 57, 58.

As is apparent from the foregoing description, the helical compression spring 61 housed in the skirts 37, 53 is held between the circular flange of the skirt 37 and the shoulder $54'$ at the lower end of the threaded hole 54 so that the valve body assembly 40 is normally forced upwardly, and the shoulder 44 of the main valve body 41 abuts against the undersurface of the circular flange of the skirt 37 of the clamping bolt 36.

In the position shown in FIG. 2, the valve body assembly 40, on the one hand, maintains the outer air channel 58 and the outlet side joint pipe $14_1'$ in communication via the annular groove 48, and on the other hand, interrupts the communication between the annular groove 49 and the outlet side joint pipe $15_1'$, although maintaining the communication between the former and the intake side joint pipe $15_2'$.

When the pushbutton 51 is depressed against the spring 61 until the downwardly movement of the pushbuton 52 is stopped by the clamping bolt 36, then the annular groove 48 is misaligned with the outlet side joint pipe $14_1'$ so as to interrupt the communication between the latter and the outer air channel 58, and simultaneously the annular groove 49 is brought into alignment with the outlet side joint pipe $15_1'$ while maintaining the communication between the annular groove 49 and the intake side joint pipe $15_2'$ so that the outlet side and the intake side joint pipes $15_1'$, $15_2'$ communicate via the annular groove 49.

In the operation of the air feed-water feed control device having a construction as described above, when the insertion section 12 of the endoscope is inserted into the body cavity while leaving the regulating valve means 20 in the position shown in FIG. 2 and the air supply and water supply in the control unit are started, the air supplied to the valve casing 30 at its bottom is exhausted into the atmosphere from the vent opening 60, after passing through the inner channel 57 for air inflow of the valve body 41. At this time, the resistance of the inner air channel 57 to air flow has no effect upon the air in the outer air channel 58 at all. Moreover, a significant effect which, under certain circumstances, occurs along with the exhaust is that the air in the outer air channel 58 is withdrawn by suction and thereby removed through the vent opening 60. These effects result from the provision of the inner and outer air channels 57, 58 communicating via the communication hole 59 in the vicinity of the vent opening 60. Consequently, there is no air flow in the outlet air pipe $14_1$, so that no air is fed into the body cavity from the air feedwater feed nozzle 13 at all.

When it is intended to feed air into the body cavity, the vent opening 60 is closed by putting an operator's finger bulb on the pushbutton 51 without depressing it. As a result, the pressure of the air in the space at the bottom of the valve casing 30 increases, so as to force out the air in the inner air channel 57 into the outer air channel 58 through the communication hole 59, and thence into the outlet air pipe $14_1$. Consequently, air is continuously fed into the body cavity.

In the same manner as in conventional air feed control devices, by gradually opening the vent opening 60 by moving the finger bulb either upwardly or laterally, the quantity of air which escapes into the atmosphere from the opened vent opening can be gradually increased.

When it is required to feed water into the body cavity, the pushbutton 51 is depressed and moves downwardly the valve body assembly 40 in order to establish communication between the intake and outlet water pipes $15_1$, $15_2$ via the annular groove 49. In this way, water is conveyed from the intake water pipe $15_2$ to the outlet water pipe $15_1$ through the annular groove 49 and thence fed into the body cavity from the air feed-water feed nozzle 13. Since the annular groove 48 is misaligned with the joint pipe $14_1'$ coupled to the outlet air pipe $14_1$, air feed into the body cavity is completely interrupted.

Figure 3:
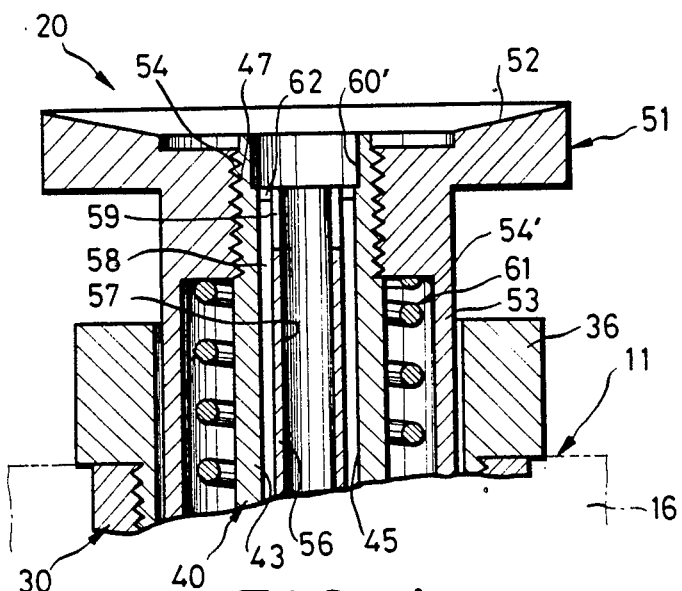
FIG. 3 is a longitudinal sectional view, taken along the vertical plane III—III of FIG. 4, of a second embodiment of an air feed control device in accordance with the present invention, this view being similar to FIG. 2, and, however, showing mainly that part of the regulating valve means which is different from that of FIG. 2.
Figure 4:
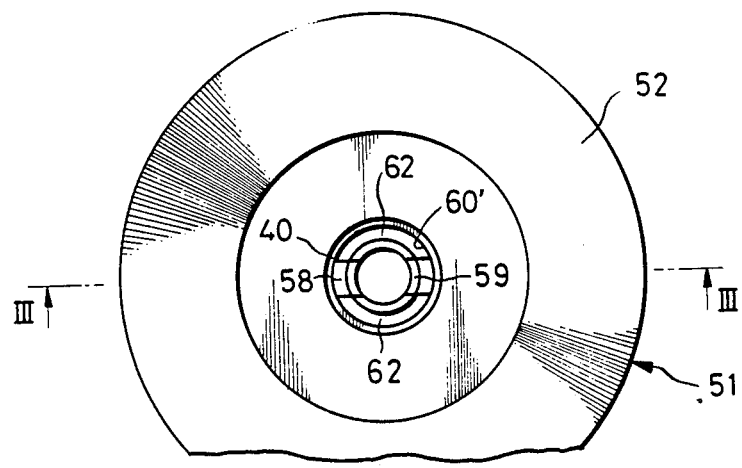
FIG. 4 is a plan view of the regulating valve means of FIG. 3.
Figure 5:
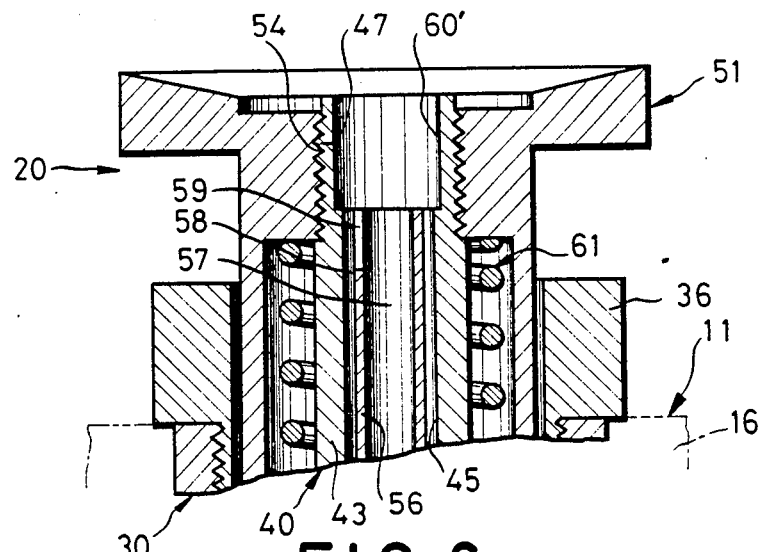
FIG. 5 is a longitudinal sectional view of a third embodiment of an air feed control device in accordance with the present invention, this view being similar to FIG. 3.
Figure 6:
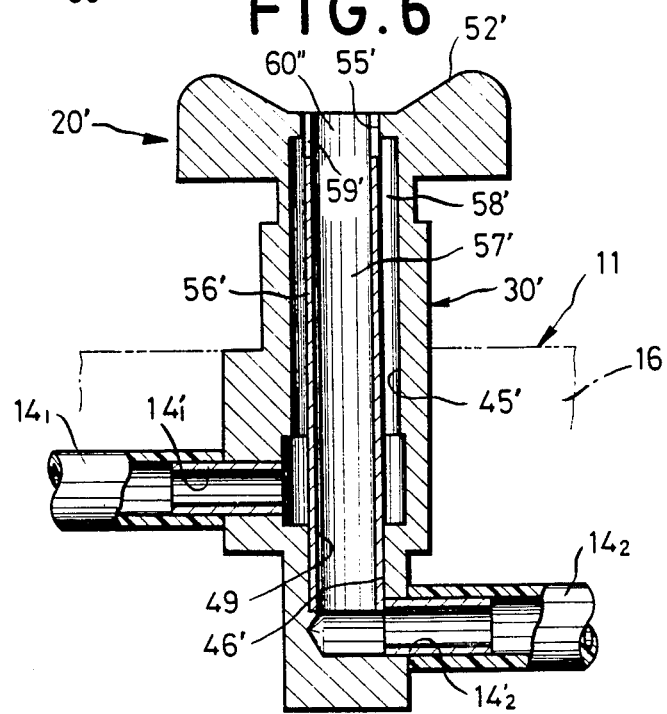
FIG. 6 is a longitudinal sectional view of a fourth embodiment of an air feed control device in accordance with the present invention.

FIGS. 3 to 5 illustrate air feed-water feed control devices according to second an third embodiments; and FIG. 6 illustrates an air feed control device according to a fourth embodiment.

In these embodiments, most of the components are similar to if not identical with those of the first embodiment. For this reason, these components are omitted or designated by the same reference numerals as before.

The second embodiment shown in FIGS. 3 and 4 is distinguished from the first by the fact that provision is made for part-circular spacers 62. The regulating valve means 20 has a valve body assembly 40 which is slightly modified in the upper valve portion 43, which in this instance, has an extended top end provided with external threads 47 which is directly engaged with the internal threads 54 of the pushbutton 51 so as to open to the atmosphere to serve as a vent opening $60'$. On the contrary, there has been omitted from the upper end of the cylindrical partition wall 56 the part which corresponds to that portion of the partition wall which was fitted into the openings 55 formed in the T-shaped member 52 shown in FIG. 2. The top end of the partition wall 56, in which are formed vertical notches 59 as a result of cutting off said part, is fixed to the inner wall of the upper valve portion 43 by means of part-circular spacers 62 attached therebetween.

The third embodiment shown in FIG. 5 is distinguished from the second embodiment shown in FIGS. 3 and 4, solely in that the semi-circular spacers 62 have been eliminated. The cylindrical partition wall 56 is supported only by fitting its bottom end into the reduced inner diameter of bore 46 of the main valve body 41, as in the first embodiment.

Finally, reference is had to FIG. 6, in which is shown an air feed control device according to a fourth embodiment of this invention in which a regulating valve means 20' has no valve body assembly or coil spring or parts relevant thereto as in the regulating valve means shown in FIGS. 2 to 5, but rather comprises a valve casing 30' having the shape of a barrel having an axial cylindrical bore 45', and a cylindrical partition wall 56' fitted in the lower part 56' of the cylindrical bore 45' and having a reduced diameter so as to divide the inside of the cylindrical bore into two spaces, namely, inner and outer air channels 57', 58'.

The valve casing 30' is provided with joint pipes $14_1'$, $14_2'$ with which the outlet air pipe $14_1$ and the outer air channel 58', and the intake air pipe $14_2$ and the inner air channel 57', respectively, communicate. The valve casing 30' further has at its top a fingerpiece 52' provided with a vent opening 60" which has the same inner diameter as the lower bore portion 46' and in which the top end of the cylindrical partition wall 56' provided with longitudinal notches 59' is fitted.

The air feed-water feed control devices according to the second and third embodiments can be operated in quite the same way as the first one with the same results. Furthermore, the air feed control devices according to the fourth embodiment can also be operated in quite the same way as the first embodiment of the air feed control device with the same result.

It should be noted that the cylindrical partition walls 56, 56' may be replaced with a partition plate in order to provide in the regulating valve means inflow and outflow air channels.

While preferred embodiments of the present invention have been described, it is to be understood that modifications and changes will be apparent to those skilled in the art without departing from the spirit of the invention.

The scope of the invention, therefore, is to be determined solely by the following claims.

What is claimed is:

1. In an air feed control device of an endoscope comprising regulating means mounted in an operating section of the endoscope, which means is provided with a vent hole opening to the atmosphere for regulating the quantity of air escaping therethrough into the atmosphere and by which means an intake air pipe having one end adapted to be connected to an air supply separate from the endoscope and an outlet air pipe having one end connected to an air feed nozzle at the distal end of an insertion section of the endoscope are connected in communication with each other; the improvement in which said regulating means includes therein an inflow air channel for connecting said vent hole with said intake air pipe and an outflow air channel for connecting said vent hole with said outlet air pipe, and inflow and outflow air channels being in communication with each other only in the vicinity of the point at which said vent hole opens to the atmosphere said regulating means comprising a hollow body having a cylindrical axial bore and a partition wall for dividing said cylindrical bore into two air channels for inflow and outflow.

2. A device as defined in claim 1, wherein said partition wall is cylindrical and coaxial with said cylindrical bore so as to divide said cylindrical bore into inner and outer air channels.

3. In a control device of an endoscope for selectively feeding air and water and regulating the quantity of air to be fed into a cavity, said device comprising means mounted in an operation section of the endoscope for allowing selectively air and water to flow therethrough as well as for regulating the quantity of air escaping therefrom when air flow is selected, a nozzle disposed at the distal end of an insertion section of the endoscope insertable into a said cavity for feeding air and water therethrough into the cavity, an air conduit for conducting air from an air supply separate from the endoscope to the nozzle through said means, and a water conduit for conducting water from a water supply separate from the endoscope to the nozzle through said means; the improvement in which said means comprises a valve casing having the shape of a barrel having an axial cylindrical bore having an end that is open to the atmosphere, a valve body supported airtightly in said bore for sliding movement between air flow and water flow positions, said valve body having air inflow and outflow channels therein which communicate with each other only in the vicinity of said open end, and resilient means for forcing said valve body in a direction out of the bore toward said air flow position.

4. A control device as claimed in claim 3, wherein said valve body comprises a hollow body penetrated by a cylindrical bore and a partition wall provided in said cylindrical bore by which said cylindrical bore is divided into two channels for air inflow and air outflow respectively.

5. A control device as claimed in claim 4, wherein said partition wall is a cylindrical partition wall for defining an inner channel for air inflow and an outer channel for air outlfow.

6. A control device as defined in claim 5, wherein said valve body is provided around its outer periphery with an annular groove which communicates with said outer channel and with which said air conduit communciates only in said air flow position.

7. A control device as defined in claim 6, wherein said resilient means consists of a helical compression spring in compression between said valve casing and valve body.

8. A control device as defined in claim 7, wherein said cylindrical partition wall has its one end fitted in a reduced diameter of opening at the end of said cylindrical bore of said valve body.

9. A control device as defined in claim 8, wherein said cylindrical partition wall has at least one opening which provides the communication between said inner and outer channels.

10. A control device as defined in claim 7, wherein said cylindrical partition wall has its one end fixed to the inner wall of said cylindrical bore of said valve body by means of spacers.

11. A control device as defined in claim 7, wherein said cylindrical partition wall has its one end opening into said cylindrical bore of said valve body.

* * * * *